United States Patent [19]
Hagiwara et al.

[11] Patent Number: 5,321,495
[45] Date of Patent: Jun. 14, 1994

[54] OPTICAL DETECTING SYSTEM FOR DETERMINING PARTICLE POSITION ON A SUBSTRATE

[75] Inventors: Takashi Hagiwara; Minoru Taniguchi; Dainichiro Kinoshita, all of Miyanohigashi, Japan

[73] Assignee: Horiba, Ltd., Kyoto, Japan

[21] Appl. No.: 921,923

[22] Filed: Jul. 29, 1992

[30] Foreign Application Priority Data

Jul. 30, 1991 [JP] Japan .................. 3-212844

[51] Int. Cl.[5] .......................................... G01N 21/00
[52] U.S. Cl. ............................... 356/237; 250/561; 250/236; 250/563; 356/431
[58] Field of Search .............. 356/237, 431; 250/563, 250/572, 561, 236

[56] References Cited

U.S. PATENT DOCUMENTS

| | | | |
|---|---|---|---|
| 4,468,120 | 8/1984 | Tanimoto et al. | 356/237 |
| 4,610,541 | 9/1986 | Tanimoto et al. | 356/237 |
| 4,803,367 | 2/1989 | Murase et al. | 250/236 |
| 4,829,175 | 5/1989 | Goto et al. | 250/236 |
| 4,889,998 | 12/1989 | Hayano et al. | 250/563 |
| 4,898,471 | 2/1990 | Stonestrom et al. | 356/237 |
| 4,902,131 | 2/1990 | Yamazaki et al. | 356/237 |
| 4,950,889 | 8/1990 | Budd et al. | 250/236 |
| 4,982,105 | 1/1991 | Takahashi | 250/563 |
| 4,999,510 | 3/1991 | Hayano et al. | 250/571 |

Primary Examiner—Robert J. Warden
Assistant Examiner—Hien Tran
Attorney, Agent, or Firm—Price, Gess & Ubell

[57] ABSTRACT

An apparatus for detecting particles on a substrate incorporates a calibration system to correct any change in the angle of swing of a beam scanning mirror over a period of time. A pair of optical detectors can be positioned within the optical path between the scanning mirror and the substrate to provide a fixed reference point from which positional adjustments or calibrations can be made over the life of the instrument to eliminate any drifting of the positional signals of the actually detected particles on the substrate.

8 Claims, 3 Drawing Sheets

OPTICAL DETECTING SYSTEM FOR DETERMINING PARTICLE POSITION ON A SUBSTRATE

BACKGROUND OF THE INVENTION

1. Field of the Invention

The present invention relates to an apparatus for detecting particles that may be stuck on the surfaces of substrates, for example, reticles and masks used for producing printed circuit patterns on semiconductor wafers, such as in the production of LSI (large-scale integrated) product wafers, or substrates that are used in liquid crystal displays, and more particularly, to an optical system for specifying a size of the particles and a location on a substrate where the particles are adhered.

2. Description of Related Art

Referring to FIG. 2, a conventional apparatus for detecting particles is disclosed. A substrate 1, for example, a substrate provided with a circuit pattern formed on a surface thereof, can be aligned horizontally on an inspection stage (not shown) and provided with a pellicle frame 2 on an upper surface thereof. The substrate 1 is adapted to be slidably moved in both the directions shown by the arrow X and arrow Y to enable positional alignment on the inspection stage.

An optical system 3, which can include an He-Ne laser cavity 4 for transmitting a laser beam L, having an appointed angle of polarization, is provided with a beam expander 5. The expanded laser beam L contacts a beam scanning mirror 6, for example, a galvanomirror, that can revolve in the direction indicated by the arrows U-V, to enable the laser beam L to be scanned through a lens 7. The lens 7 permits the laser beam L to be incident upon the surface of the substrate to be inspected. Thus, a linear scanning in the direction shown by the arrow X will occur so that the laser beam, generated from the laser cavity 4, will be irradiated on the substrate to be inspected from an appointed or predetermined angle relative to the vertical plane with a reciprocation of a linear scanning within an appointed or predetermined range in the direction shown by the arrow X.

A detector optical system 8 is arranged at both ends of the substrate in the X-direction and is also inclined to the plane of the substrate. Each of these optical systems includes a collecting lens 9, a fixed slit aperture plate 11, having a long and slender slit 10 in the vertical direction for limiting an incidence of a reflected and scattered beam R which has been reflected and scattered from the particles on the surface of the substrate to be inspected. An optical detector 12 is capable of receiving the laser beam L which has been incident upon the substrate and reflected or scattered from the particles. The optical detector 12 can comprise, for example, a photomultiplier tube and the like for detecting the reflected scattered beam R.

In operation, the laser beam L is incident upon the substrate at the predetermined angle and linearly moves across the inspection stage in the direction shown by the arrow Y, while reciprocally and linearly scanning within the predetermined range in the direction shown by the arrow X. As a result, a reflected and a scattered beam R is reflected and scattered from the particles on the substrate to be inspected and is detected by the optical detector 12. If any particles exist on the surface of the reciprocating substrate to be inspected and is contacted by the laser beam L, it is capable of scattering the laser beam at random in all directions, which will impact the intensity of light measured by the optical detector 12. Correlating the incident of detection with the spatial position of the substrate will indicate the existence of a particle on the surface of that substrate at that location.

As can be appreciated, a close correlation between the actual position of the laser beam L on the substrate surface is necessary for accurately determining the position of any particle. If any deviation is provided in the relationship between the angle of swing of the beam scanning mirror 6, which reciprocally scans the laser beam L transmitted by the laser cavity 4, and the angle of the swing signal put out from the beam scanning mirror 6 on account of any drift in the electrical system resulting from an influence by temperature, or an aging of the circuit parts, or a variation in tolerances of the circuit parts and the like, then a lapse of time occurs, which will correspondingly create an error in determining the accurate position of any particle.

Referring to FIG. 3, when the electrical system does not exhibit any drift and is accurately correlated with the position of the laser beam, then a linear relationship is maintained between the position of the particles obtained by calculation on the basis of the scanning position signals (angle of swing signals) and the actual position of particles. This relationship is shown as a straight line I in FIG. 3. As can be determined, the calculated position of particles corresponding, for example, to particle A and particle B will amount to SA and SB, respectively, and accordingly the positions of the particles A and B can be detected and accurately reproduced for subsequent visual examination purposes. However, if any drift in the electrical system or other error occurs, a deviation, D, can be produced in the relationship between the calculated positions of the particles and the actual position of the particles. Thus, the calculated position of particles corresponding to particles A and B can apparently occur at positions SA' and SB' by incorporating the deviational error D. It is possible that temperature changes can be minimized by the incorporation of a temperature compensation feature into the circuit driving the beam scanning mirror 6, but it is extremely difficult to account for aging and tolerance changes of circuit components and the like that can occur over a period of time with the use of the instrument.

Thus, there is a demand in the prior art to provide a relatively improved economical particle detecting system.

SUMMARY OF THE INVENTION

The present invention has been achieved by paying attention to the above described problems experienced in the prior art. It is an object of the present invention to provide an apparatus for detecting particles which provides corrections in the change of angles in the swing of the beam scanning mirror over a period of time to improve the accuracy of the detected positions of particles so that their positions can be faithfully reproduced for inspection purposes.

The present invention provides an apparatus for detecting particles with an incident optical system positioned between a beam scanning mirror and a lens or between the lens and a substrate to be inspected. The optical system includes two optical detectors for use in monitoring the scan path of the laser beam appropriately positioned at suitable intervals in a scanning directional laser beam. Any differences determined in this optical path between an angle of a swing signal of the beam scanning mirror and a position signal of an optical detector can be automatically corrected so that the detected position of a particle can be appropriately compensated.

By providing two optical detectors arranged at suitable intervals in the scanning directional laser beam, it is possible to establish standard points that are fixedly provided relative to the laser beam to be scanned, which will not change over a period of time. Thus, any change of the relationship between the angle of the swing signal of the beam scanning mirror and the position of the optical detector for use in monitoring the laser beam, while scanning the substrate surface can be determined by these optical detectors to define any deviation resulting. A microprocessor circuit can employ a computer program to automatically determine the quantity of deviation and to automatically correct for the detected position of any particle detected.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved optical particle detector.

Figure 1:
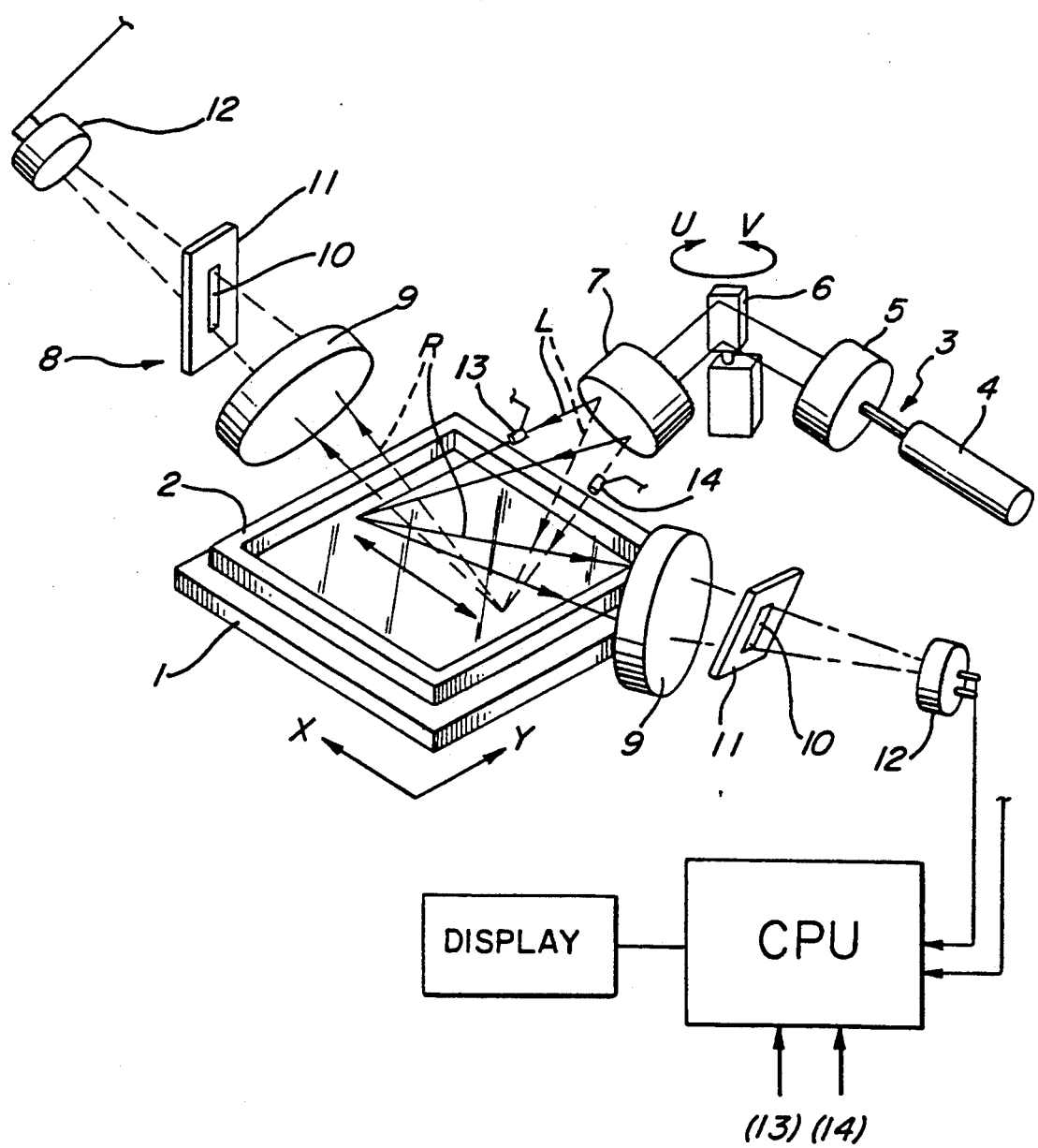
FIG. 1 is drawing schematically showing the preferred embodiment of the present invention.
Figure 2:
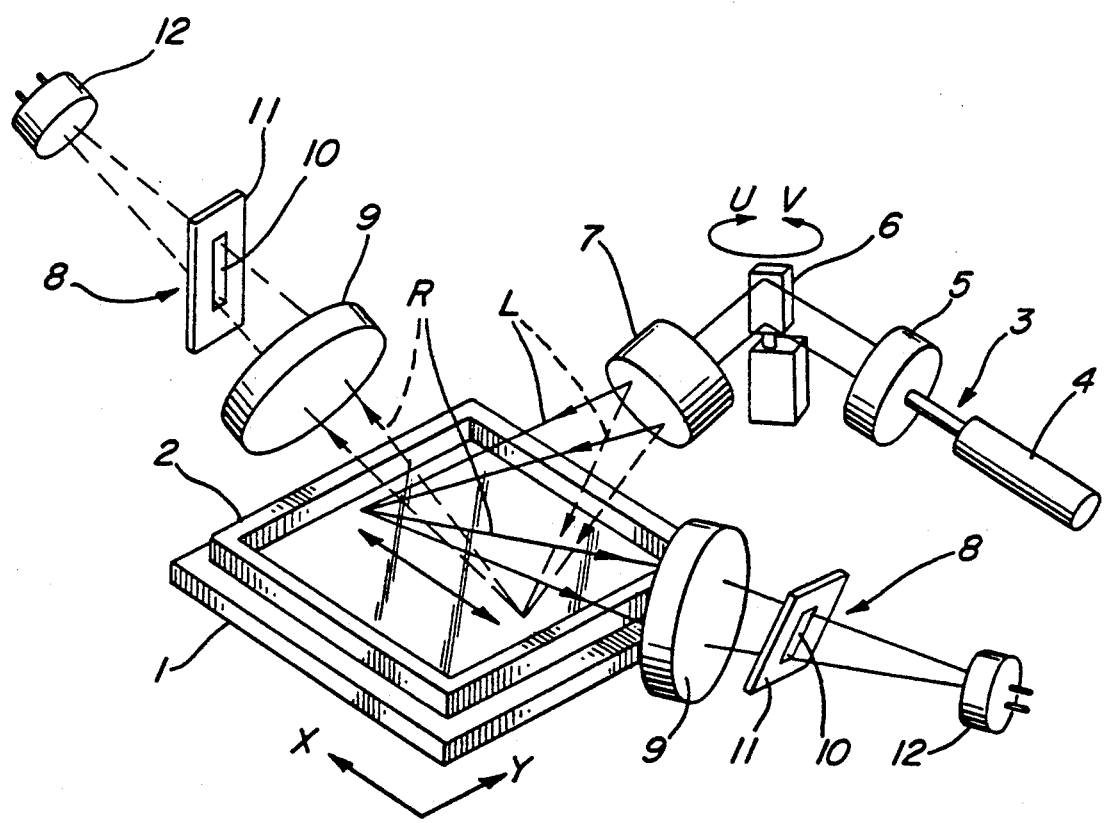
FIG. 2 is a schematic perspective view showing the construction of a conventional apparatus for detecting particles.

Referring to FIG. 1, a schematic perspective view of the apparatus of the present invention for detecting particles on a substrate is shown. Referring to the elements in FIG. 1, common elements from FIG. 2 utilize the same reference numbers.

Figure 3:
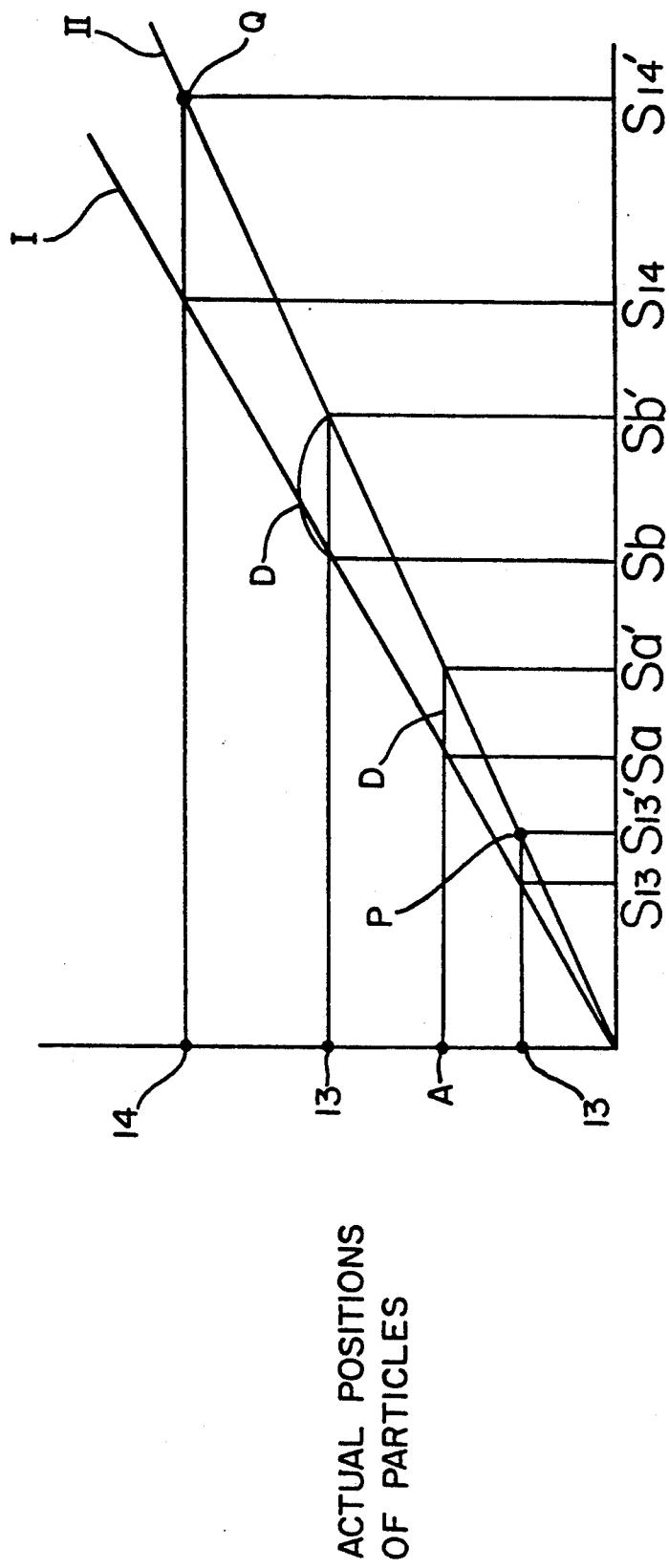
FIG. 3 is a schematic chart disclosing a graph of the problems to be solved by the present invention.

In this regard, a laser beam L is appropriately scanned across a substrate 1 by revolving a mirror 6, while the substrate is moved through the scan line in the Y direction. Between the lens 7 and the substrate 1 a pair of optical detectors 13 and 14 is inserted into the optical system to act as scanning monitors. These optical detectors can, for example, be pin photodiodes. These pin photodiodes 13 and 14 are arranged at a suitable interval in a scanning direction X of the laser beam L. These photodiodes 13 and 14 can be conceptionally thought of as fixed reference points relative to the substrate 1. For example, the pin photodiodes 13 and 14 can be deemed as hypothetical particles which will exist at fixed positions on each substrate. Referring, for example, to FIG. 3, numerals 13 and 14 on an axis of the ordinate show the existing positions of the pin photodiodes 13 and 14. In the case where the angle of the beam swinging mirror 6 is not changed with the lapse of time, a scanning position signal of the laser beam L will be detected by one pin photodiode 13 when the beam scanning mirror is revolved by a certain angle in the direction shown by the arrow U. This position is S13. Additionally, a scanning position signal of the laser beam L can be detected by the other pin photodiode 14 when the beam scanning mirror 6 is revolved by a certain angle in a direction shown by the arrow V as S14.

If the angle of swing of the beam scanning mirror 6 is changed over a lapse of time, the scanning positional signal, which would be measured corresponding to the pin photodiode 13 and 14, becomes S13' and S14', respectively. As can be seen from FIG. 3, a point of intersection P of an extension parallel to an axis of the abscissa from a position of the pin photodiode 13 and an extension parallel to the axis of the ordinate from the scanning position signal S13' can be connected with a point of intersection Q of a corresponding extension parallel to the axis of abscissa from a position of the pin photodiode 14 and also a corresponding extension parallel to the axis of ordinate from the scanning position signal to obtain a straight linear line II. Any difference between this straight line II and the straight line I (designated by reference number D in FIG. 3) shows the quantity of deviation based on the change of the beam scanning mirror 6. As can be appreciated, the detected position of the particle based on this relationship can be automatically corrected to accurately define any detected particles, e.g., particles A and B. Thus, the pin photodiodes 13 and 14 effectively provide fixed reference coordinates from which an automatic calibrated correction can be accomplished. The coordinates, for example, of the straight line I can be determined as the initial reference and the subsequent measurements of the pin photodiodes 13 and 14 can be utilized to calculate the necessary deviation corrections to the actual position of any particles on a substrate surface. During manufacturing of the instrument, the line I of FIG. 3 is established with the optical detectors 13 and 14 aligned. The coordinates of the reference line I are stored in a memory and used as a reference point or datum line from which to determine the percentage of any deviation based on actual measurements from the optical detectors 13 and 14. The optical detectors 13 and 14 will constantly monitor the scan line at every cycle, while the optical detector 12 will respond when particles are detected. The particle position is then corrected on the basis of the detected result and the angle of the swing signal of the mirror 6. A computer circuit, CPU, can receive both the output of the optical detectors 12, 12 and the pin photodetectors 13 and 14 and can both compute a particle position and the appropriate correction.

Although the pin photodiodes 13 and 14 are arranged in the optical path of the incident optical system 3 between the lens 7 and the substrate to be inspected 1, it is possible in an alternative arrangement for these coordinate points or reference points to be arranged in the optical path of the incident optical system 3 between the beam scanning mirror 6 and the lens 7, since the functioning of the lens 7 will be constant and will not alter over a time period.

In accordance with the present invention, any change in the difference between the angle of swing of the swing signal of the beam scanning mirror 6, scanning the laser beam and the actual angle of swing resulting from a lapse of time can be compensated through the use of pin photodiodes and, therefore, the actual detected positions of particles on the substrate can be automatically corrected on the basis of this calibration system.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A particle detecting apparatus for detecting particles on an object comprising:
    means for scanning an object with a light beam along scan lines;
    detecting means for detecting light from the object which has been incident from the scanned light beam;
    positioning means, connected to the detecting means, for determining any variation in detected light indicative of particles on the object to determine the existence of a particle and the particle position;
    reference means for providing fixed reference points relative to the scan line of the light beam; and
    means for compensating for the detected position of the particle, from the positioning means, and the actual position of the particle based on the fixed reference points from the reference means.

2. The apparatus of claim 1 wherein the reference means for providing fixed reference points includes a pair of photodetectors positioned within an optical path of the scanning light beam.

3. In a particle detecting apparatus for determining the position of minute particles on a substrate having a laser beam scanning across the substrate in an optical path and moving relative to the substrate and detector means for sensing laser light after incidence on the substrate to enable the determination of any particle position, the improvement comprising:
    compensation means includes a sensor in the optical path of the laser beam to detect the scanned laser beam for providing compensation to an output of the detector means to ensure an accurate determination of the position of any minute particle.

4. The invention of claim 3 where the sensor of the compensation means includes a pair of optical detectors.

5. The invention of claim 4 wherein a scanning mirror scans the laser beam and a lens directs the laser beam to be incident on the substrate, the optical detectors are positioned between the lens and the substrate.

6. The invention of claim 4 wherein a scanning mirror scans the laser beam and the optical detectors are positioned between the scanning mirror and the substrate at fixed positions along the scan line.

7. A laser beam particle detecting apparatus for automatically detecting the position of minute particles on a semiconductor substrate to enable a subsequent visual inspection, comprising:
    means for supporting a substrate;
    means for scanning a laser beam in a predetermined optical scan path across the substrate including a scanning mirror for directing the scanning laser beam at an acute angle to a surface of the substrate;
    detecting means for optically detecting the laser beam after incidence with the substrate including a pair of optical detectors and a pair of masked aperture plates positioned adjacent to the substrate and on either side of the means for scanning, to define a position of a particle;
    a pair of detectors positioned to intercept the predetermined optical scan path at predetermined fixed points to define reference points; and
    compensation means, connected to the detecting means and the pair of detectors, for compensating for the detected position of a particle.

8. The invention of claim 7 wherein the compensation means includes means for comparison of a predetermined stored linear relationship of the scanning laser beam and a derived linear relationship from the reference points of the pair of detectors to determine any deviation in particle position on the substrate.

* * * * *

UNITED STATES PATENT OFFICE
CERTIFICATE OF CORRECTION

Patent No. 5,321,495          Dated   June 14, 1994

Inventor(s)  Takashi Hagiwara et al.

It is certified that error appears in the above-identified patent and that said Letters Patent is hereby corrected as shown below:

On the cover page, after "[73] Assignee:   Horiba, Ltd., Kyoto, Japan" insert:

--and Hitachi, Ltd., Tokyo, Japan--.

Signed and Sealed this

Seventh Day of March, 1995

Attest:

BRUCE LEHMAN

*Attesting Officer*          *Commissioner of Patents and Trademarks*